United States Patent [19]

Rideout et al.

[11] Patent Number: 5,156,744
[45] Date of Patent: Oct. 20, 1992

[54] PROCESS FOR INHIBITING SCALE USING MALEIC ANHYDRIDE POLYMERIZED IN REACTIVE AROMATIC HYDROCARBONS

[75] Inventors: Jan Rideout, Horwich; Duncan J. MacQuarrie, Cheadle, both of England

[73] Assignee: FMC Corporation, Philadelphia, Pa.

[21] Appl. No.: 766,495

[22] Filed: Sep. 26, 1991

Related U.S. Application Data

[62] Division of Ser. No. 476,208, Feb. 7, 1990, Pat. No. 5,077,364.

[30] Foreign Application Priority Data

Feb. 14, 1989 [GB] United Kingdom ............... 8903330
Nov. 24, 1989 [GB] United Kingdom ............... 8926586

[51] Int. Cl.$^5$ ............................................. C02F 5/08
[52] U.S. Cl. ....................................... 210/698; 252/180
[58] Field of Search .................... 210/698; 252/180; 526/271; 549/252

[56] References Cited

U.S. PATENT DOCUMENTS

| | | | |
|---|---|---|---|
| 3,320,216 | 5/1967 | Butler | 526/286 |
| 3,474,114 | 10/1969 | Kuhlkamp et al. | 549/252 |
| 3,810,834 | 5/1974 | Jones et al. | 210/698 |
| 3,919,258 | 11/1975 | Richardson et al. | 549/252 |
| 4,212,788 | 7/1980 | Birrell et al. | 526/271 X |
| 4,374,733 | 2/1983 | Snyder et al. | 210/701 |
| 4,789,716 | 12/1988 | Scholz | 526/201 |
| 4,818,795 | 4/1989 | Denzinger et al. | 525/327.8 |

FOREIGN PATENT DOCUMENTS 971731 10/1964 United Kingdom .
1193146 5/1970 United Kingdom .

*Primary Examiner*—Joseph L. Schofer
*Assistant Examiner*—M. Nagumo
*Attorney, Agent, or Firm*—Patrick C. Baker

[57] ABSTRACT

Polymaleic anhydride having a weight average molecular weight by gel permeation chromatography of between 450 and 800 and a polydispersivity of between 1.0 and 1.15 is produced by polymerizing maleic anhydride, using a peroxide initiator in an amount not greater than 10% by weight of the anhydride, in a dilute solution in o-xylene or a substituted o-xylene.

9 Claims, No Drawings

PROCESS FOR INHIBITING SCALE USING MALEIC ANHYDRIDE POLYMERIZED IN REACTIVE AROMATIC HYDROCARBONS

This is a divisional of application Ser. No. 476,208, filed Feb. 7, 1990, now U.S. Pat. No. 5,077,364, issued on Dec. 31, 1991.

The present invention relates to the polymerisation of maleic anhydride and products of such polymerisation.

It is well known that maleic anhydride can be polymerised to give polymers of varying molecular weights, several methods of polymerisation having been described in the literature. The use of these polymers and other polycarboxylic acids as scale control agents in aqueous systems is well established.

Methods of polymerisation using toluene or xylene solvents are known, but generally require large amounts of initiator, e.g. 15-30% and concentrated solutions of monomer in the solvent to produce reasonable yields of polymer. GB 1411063 describes the use of xylene having an ortho-isomer content not greater than 99%. The molecular weight distribution of the products produced by these processes is usually quite large.

We have now surprisingly found that when polymerisation is carried out using a dilute solution of maleic anhydride in ortho-xylene or a substituted ortho-xylene and using low initiator levels, a good yield of product is obtained, which has a narrow molecular weight distribution and shows superior activity as a scale control agent compared with known polycarboxylic acid scale control agents. The products contain novel polycarboxylic acid anhydrides which can be isolated if desired and which can be hydrolysed to give the corresponding novel polycarboxylic acids or water-soluble salts thereof. The novel materials have surprisingly high activity as scale control agents.

Accordingly the present invention provides a polymaleic anhydride having a weight average molecular weight by gel permeation chromatography (GPC) of between 450 and 800 and a polydispersivity of between 1.0 and 1.15.

Polydispersivity is the ratio $M_w/M_n$ where $M_w$ is the weight average molecular weight and $M_n$ is the number average molecular weight.

The polymaleic anhydride of the present invention may be produced by polymerising maleic anhydride, using a peroxide initiator in an amount not greater than 10% by weight of the anhydride, in a solvent which is predominantly an o-xylene of formula I:

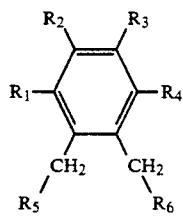

where $R_1$, $R_2$, $R_3$ and $R_4$ each independently denote a hydrogen atom, a $C_1$-$C_4$ alkyl group or a carboxyl group; $R_5$ and $R_6$ each independently denote a hydrogen atom or a methyl group, or $R_5$ and $R_6$ together denote a methylene or ethylene group; the weight ratio of maleic anhydride to solvent being not greater than 1:3, most preferably not greater than 1:4.

The amount of peroxide initiator may be from 1-10%, preferably 4 to 8%, by weight based on the maleic anhydride. The initiator may be chosen from known peroxide initiators. For example, it may be dibenzoyl peroxide, tert. butyl perbenzoate, dicumyl peroxide, tert. butyl hydroperoxide or, preferably di-tert.butylperoxide.

The weight ratio of maleic anhydride to solvent may be from 1:3 to 1:9, preferably from 1:3 to 1:6 and especially from 1:4 to 1:6. This weight ratio may be higher, for example as high as 1:2, at the commencement of the polymerisation reaction, provided maleic anhydride is added during the reaction so that the final ratio is not greater than 1:3.

The polymerisation, which may be effected batchwise or continuously, may be carried out at a temperature from 100° to 200° C., preferably at or near the reflux temperature of the solvent, which in practice is usually within the range 120° to 160° C., for example 120° to 146° C. The reaction time may vary according to the reaction temperature and the nature of the initiator used. When polymerisation is effected using di-tert.butyl peroxide in refluxing o-xylene, the reaction time is usually between 2 and 5 hours.

The solvent preferably contains at least 90% by weight of one or more compounds of formula I, more preferably greater than 95%, most preferably at least 97%, by weight of such compounds. The solvent may contain minor amounts of other xylene isomers and ethylbenzene.

Polymerisation as hereinbefore described results in a polymaleic anhydride product containing isolatable novel polycarboxylic acid anhydrides, usually in admixture with other polycarboxylic acid anhydrides. Accordingly, the present invention also provides a polycarboxylic acid anhydride of formula II:

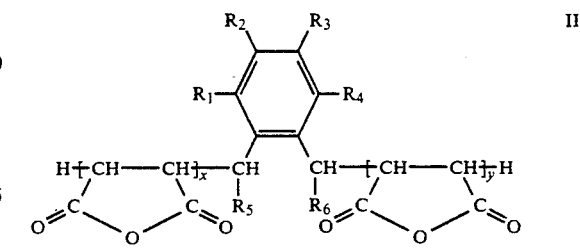

where $R_1$, $R_2$, $R_3$, $R_4$, $R_5$ and $R_6$ are as hereinbefore defined, x denotes 1, 2 or 3 and y denotes 1, 2 or 3, with the proviso that x and y are not both 1.

The anhydrides of formula II are usually obtained, as a result of the polymerisation process, in the form of novel mixtures with polycarboxylic acid anhydrides of formula III:

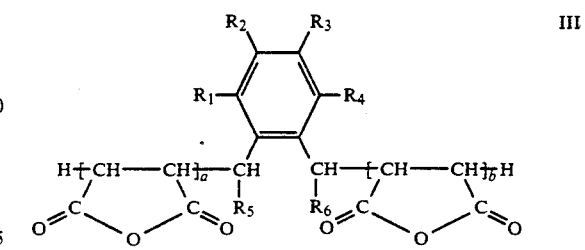

where $R_1$, $R_2$, $R_3$, $R_4$, $R_5$ and $R_6$ are as hereinbefore defined, a and b each denote 0 or 1 and the sum of a+b denotes 1 or 2. The polymerisation product may also contain minor amounts of unreacted compounds of formula I.

The mixture generally contains at least 50% of the anhydride of formula II. If the polymerisation product is worked up using procedures which remove more soluble components, the percentage amount of the anhydride of formula II in the mixture is increased.

In formulae I, II and III, when $R_1$, $R_2$, $R_3$ or $R_4$ denotes an alkyl group, it may be methyl, ethyl, n-propyl, isopropyl, n-butyl, isobutyl, sec.butyl, or tert.butyl. Preferred compounds of formulae I, II and III include those where $R_1$ to $R_6$ each denote a hydrogen atom; where $R_1$ to $R_3$, $R_5$ and $R_6$ each denote a hydrogen atom and $R_4$ denotes a methyl group; where $R_1$ denotes a methyl group and $R_2$ to $R_6$ each denote a hydrogen atom; where $R_1$, $R_4$, $R_5$ and $R_6$ each denote a hydrogen atom and $R_2$ and $R_3$ each denote a methyl group; where $R_1$, $R_2$, $R_4$, $R_5$ and $R_6$ each denote a hydrogen atom and $R^3$ denotes a methyl group; where $R_1$, $R_3$, $R_4$, $R_5$ and $R_6$ each denote a hydrogen atom and $R_2$ denotes a methyl group; where $R_1$, $R_2$, $R_4$, $R_5$ and $R_6$ each denote a hydrogen atom and $R_3$ denotes a tert.butyl group; where $R_1$ and $R_3$ to $R_6$ each denote a hydrogen atom and $R_2$ denotes a tert.butyl group; where $R_1$, $R_3$, $R_5$ and $R_6$ each denote a hydrogen atom and $R_2$ and $R_4$ each denote a methyl group; where $R_1$ and $R_3$ each denote a methyl group and $R_2$, $R_4$, $R_5$ and $R_6$ each denote a hydrogen atom; and where $R_1$, $R_4$, $R_5$ and $R_6$ each denote a hydrogen atom and $R_2$ and $R_3$ each denote a carboxyl group.

In the preferred compounds of formula II, preferably x denotes 1 and y denotes 2. The component of formula III present in the polymerisation product generally consists principally of compounds where a is 1 and b is 1.

In especially preferred embodiments of the invention, the groups $R_1$ to $R_6$ in formulae I, II and III each denote a hydrogen atom and, in formula II, x denotes 1 and y denotes 2. Thus in such embodiments the compound of formula I, i.e. the predominant compound in the polymerisation solvent, is o-xylene.

The polymerisation product generally separates out during the polymerisation reaction. It may be isolated as the anhydride (usually a mixture of anhydrides as hereinbefore described, although individual compounds can be isolated, if desired, by further purification) or may be hydrolysed to the corresponding free polycarboxylic acid form by standard methods using, for example, sodium hydroxide (followed by acidification) or water. Hydrolysis may be performed on the final reaction mixture or on the separated polymer. The product may also be isolated as a water-soluble salt, for example an alkali metal salt, an alkaline earth metal salt or an ammonium salt.

Purification of the polymerisation product to isolate individual compounds can be effected using conventional procedures, for example by conversion into a salt and repeated recrystallisation of the salt, the free acid then being regenerated, if desired, by acidification of an aqueous solution of the salt, followed by extraction with an organic solvent.

Compounds of formula II and mixtures thereof with compounds of formula III may be modified to give other compounds of formula II and mixtures thereof. For example, products containing a methyl group on the aromatic ring may be oxidised by known methods to convert the methyl group into a carboxyl group.

The products of the invention are useful for inhibiting the the deposition of scale forming the compounds from water or aqueous systems or for modifying the crystal habit and properties of precipitated materials. They are usually added to the water or aqueous system in an amount of 0.1 to 100 ppm, preferably 0.5 to 20 ppm.

When used to inhibit the deposition of scale and the precipitation of salts from aqueous solutions, the products of the invention, are particularly effective in inhibiting deposition of scale-forming salts derived from calcium, magnesium, barium or strontium cations, and anions such as sulphate, carbonate, hydroxide, phosphate and silicate.

With respect to aqueous system which may be treated according to the present invention, of particular interest are cooling water systems, steam generating systems, sea-water evaporators, reverse osmosis equipment, bottle washing plants, pulp and paper manufacturing equipment, sugar evaporator equipment, soil irrigation systems, hydrostatic cookers, gas scrubbing systems, flue gas desulphurisation systems, closed circuit heating systems, aqueous-based refrigeration systems, oil production and drilling systems, oil refineries, waste treatment plants, crystallisers, metal recovery systems and photographic developing baths.

The products of the invention may be used alone, or in conjunction with other compounds known to be useful in the treatment of aqueous systems.

In the treatment of systems such as cooling water systems, air-conditioning systems, steam-generating systems, sea-water evaporator systems, hydrostatic cookers, and closed circuit heating or refrigerant systems, corrosion inhibitors may be used such as, for example, water soluble zinc salts; phosphates; polyphosphates; phosphonic acids and their salts, for example, hydroxyethyl diphosphonic acid (HEDP), nitrilotris methylene phosphonic acid and methylamino dimethylene phosphonocarboxylic acids and their salts, for example, those described in German Offenlegungsschrift 2632774, hydroxyphosphonoacetic acid, 2-phosphonobutane-1,2,4-tri-carboxylic acid and those disclosed in GB 1572406; nitrates, for example, sodium nitrate; nitrites, e.g. sodium nitrite; molybdates, e.g. sodium molybdate, tungstates; silicates, e.g. sodium silicate; benzotriazole, bis-benzotriazole or copper deactivating benzotriazole or tolutriazole derivatives or their Mannich base derivatives, mercaptobenzotriazole; N-acyl sarcosines; N-acylimino diacetic acids; ethanolamines; fatty amines; and polycarboxylic acids, for example, polymaleic acid, polyacrylic acid, and alkali metal salts thereof, copolymers of maleic anhydride, e.g. copolymers of maleic anhydride and sulfonated styrene, copolymers of acrylic acid, e.g. copolymers of acrylic acid and hydroxyalkylated acrylic acid, and substituted derivatives of polymaleic and polyacrylic acids and their copolymers. Moreover, in such systems, the product used according to the invention may be used in conjunction with further dispersing and/or threshold agents, e.g. polymerised acrylic acid (or its salts,) phosphino-polycarboxylic acids (as described and claimed in British Patent 1458235), the cotelomeric compounds described in European Patent Application No. 0150706, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, cellulose, acrylic acid/lower alkyl hydroxy-acrylate copolymers, e.g. those described in U.S. Pat. No. 4,029,577, styrene/maleic anhydride copolymers and sulfonated styrene homopolymers, e.g. those described in U.S. Pat. No. 4,374,733 and combinations thereof. Specific threshold agents, such as for example, 2-phosphono-butane-1,2,4-tri-carboxylic acid (PBSAM), hydroxyethyl diphosphonic acid (HEDP), alkyl phosphonic acids, hydroxyphosphonoacetic acid, 1-aminoalkyl-1,1-diphosphonic acids and their salts, and alkali metal polyphosphates, may also be used.

Particularly interesting additive packages are those comprising products of the invention with one or more of polymaleic acid or copolymers thereof, especially terpolymers with ethyl acrylate and vinyl acetate, polyacrylic acid or copolymers thereof, or substituted copolymers, hydroxyphosphonoacetic acid, HEDP, PBSAM, triazoles such as tolutriazole, molybdates and nitrites.

Precipitating agents such as alkali metal orthophosphates and carbonates; oxygen scavengers such as alkali metal sulphites and hydrazines; sequestering agents such as nitrilotriacetic acid and its salts; antifoaming agents such as silicones, e.g. polydimethylsiloxanes, distearylsebacamide, distearyl adipamide and related products derived from ethylene oxide and/or propylene oxide condensations, in addition to fatty alcohols, such as capryl alcohols and their ethylene oxide condensates; and biocides, e.g. amines, quaternary ammonium compounds, chlorophenols, sulphur-containing compounds such as sulphones, methylene bis thiocyanates and carbamates, isothiazolones, brominated propionamides, triazines, phosphonium compounds, chlorine and chlorine-release agents bromine, and bromine-release agents, and organometallic compounds such as tributyl tin oxide, may be used together with products of the invention.

The invention is illustrated by the following Examples, in which percentages are by weight unless stated otherwise and in which molecular weight values $M_w$ and $M_n$ are obtained by GPC. Fast atom bombardment mass spectrometry (FAB-MS) results referred to in the Examples are obtained for the polymaleic anhydride products after their conversion into acid form by dissolution in hot water. Gas chromatography-mass spectrometry results referred to in the Examples are obtained from the trimethylsilyl ester of the polymaleic anhydride.

EXAMPLE 1

50 g of maleic anhydride and 290 g of o-xylene are heated to reflux and 3 g of di tert butyl peroxide is added in one addition over 15 minutes. The reaction is continued for 3.5 hours and the polymer allowed to separate from the solution. The reaction mixture is allowed to cool to room temperature and the liquid decanted off. 44 g of polymer is obtained (a yield of 88% based on maleic anhydride). No further purification is needed. The polymer obtained has a $M_w=550$ and $M_n=520$ giving $M_w/M_n=1.058$. GPC analysis indicates 4 components. FAB-MS identifies the major products as a compound of formula II where $R_1$ to $R_6$ are each H, $x=1$ and $y=2$ ($[M+H]^+=455$) and a compound of formula II where $R_1$-$R_6$ are each H, $x=1$ and $y=3$ ($[M+H]^+=571$).

Gas chromatography-mass spectrometry of the trimethyl silyl ester identifies the remaining components as a compound of formula III where $R_1$ to $R_6$ are each H, $a=0$, $b=1$ ($M^+=366$) and a compound of formula III where $R_1$ to $R_6$ are each H, $a=1$ and $b=1$ ($M^+=626$).

EXAMPLE 2

Example 1 is repeated except that the amount of o-xylene is 369 g. The yield of product is 42 g (84%). The product has $M_w=500$ and $M_n=480$ giving $M_w/M_n=1.04$.

EXAMPLE 3

Example 1 is repeated except that the amount of o-xylene is 255 g. The yield of product is 47.3 g (94.6%). The product has $M_w=490$ and $M_n=460$ giving $M_w/M_n=1.07$.

EXAMPLE 4

Example 1 is repeated except that the amount of o-xylene is 220 g. The yield of product is 47 g (94%). The product has $M_w=480$ and $M_n=440$ giving $M_w/M_n=1.09$

EXAMPLE 5

149.6 g of o-xylene is heated to reflux and 50.87 g of maleic anhydride is added over 1 hour. Over the same time 3.6 g di-tert-butylperoxide is also added. Reflux is continued for a further 3.5 hours, and the resulting mixture is cooled to 115° C. The liquid layer is removed to leave 47.3 g of polymerisation product, a yield of 93% based on maleic anhydride. The product has $M_w=590$, $M_n=560$ and $M_w/M_n=1.05$.

EXAMPLE 6

500 g of o-xylene is heated to reflux. 250 g of maleic anhydride and 30 g of di-tert-butylperoxide are added, in separate streams, over 2.5 hours. Reflux is continued for 1 hour and the resulting mixture is allowed to cool to 115°–120° C. 440 g of water is added over 30 minutes and the mixture is agitated for a further 15 minutes at 95° C. The mixture is then distilled until all the xylene is removed. The reaction mixture mass is adjusted to 880 g, by the addition or removal of water. 382 g of aqueous 46% NaOH solution is added, with cooling to keep the reaction temperature below 60° C. This yields 1182 g of a 38.4% solution of the sodium salt of the polymerisation product in water.

GPC analysis on the solid obtained by evaporation to dryness of the solution gives $M_w=670$, $M_n=640$ and $M_w/M_n=1.05$.

EXAMPLE 7

18.27 g of maleic anhydride and 50 g of durene (1,2,4,5-tetramethylbenzene) are heated to 140° C., and 1.1 g of di-tert-butyl peroxide is added over 5 minutes. Heating is continued at 140° C. for 3.5 hours, after which the reaction mixture is cooled to 100° C. and the liquid decanted off. The remaining solid is dissolved in dilute aqueous NaOH and the solution is washed with toluene, acidified with aqueous hydrochloric acid and evaporated to dryness. The polymerisation product (as the acid) is separated from the sodium chloride by addition of acetone and filtration. Evaporation gives the polycarboxylic acid product in a yield of 14 g, 77%. The product has $M_w=660$, $M_n=620$ and $M_w/M_n-1.06$.

FAB-MS indicates peaks for a compound of formula II where $R_1$, $R_4$, $R_5$, $R_6=H$, $R_2$, $R_3=CH_3$, $x=1$, $y=2$ at $[M+H]^+=483.1$ and a compound of formula III where, $R_1, R_4, R_5, R_6=H, R_2, R_3=CH_3, a=1, b=1$ at $[M+H]^+=367.1$.

EXAMPLE 8

15.27 g of maleic anhydride and 100 g of 1,2,3-trimethylbenzene are heated to 140° C. 0.92 g of di-tert-butyl peroxide is added over 5 minutes. The reaction mixture is heated for 3 hours at 140° C. The solution obtained is cooled to 100° C. and the liquid decanted off. The polymerisation product is placed in a vacuum oven at 50°C. for 5 hours to give a product yield of 8.98 g (59% based on maleic anhydride). The product has $M_w=646, M_n=613 \ M_w/M_n$-1.05.

FAB-MS shows peaks for a compound of formulae II and III where $R_1,=CH_3, R_2$-$R_6=H$ and $R_1$-$R_3=H, R_4=CH_3, R_5, R_6=H$, of formula II where $x=1, y=3$ at $[M+H]^+=585.1$; of formula II where, $x=1, y=2$ at $[M+H]^{30}=469.1$ and of formula III where $a=1, b=1$ at $[M+H]^+=353.1$.

EXAMPLE 9

Example 8 is repeated, except that 1,2,4-trimethylbenzene is used in place of 1,2,3-trimethylbenzene. The product yield is 12.51 g, 82% based on maleic anhydride. GPC analysis gives $M_w=638, M_n=616$ and $M_w/M_n=1.036$.

FAB-MS shows peaks for compounds of formula II where $R_1=H, R_2=CH_3, R_3$-$R_6=H$ and where $R_1, R_2=H, R_3=CH_3, R_4$-$R_6=H$, both for $x=1, y=2$ at $[M+H]^+=469.0$.

EXAMPLE 10

Example 7 is repeated using 20 g of maleic anhydride, 80 g of isodurene (1,2,3,5-tetramethylbenzene) and 1.2 g of di-tert-butylperoxide in place of the mixture used in Example 7. The yield of product is 21.2 g, 106% based on maleic anhydride. The product has $M_w=689, M_n=657$ and $M_w/M_n=1.048$.

FAB-MS shows peaks for compounds of formulae II and III where $R_1, R_3=CH_3, R_2, R_4$-$R_6=H$ and $R^1=H, R_2, R_4=CH_3, R_3, R_5, R_6=H$; of formula II where $x=1, y=2$ at $[M+H]^+=483.1$; and of formula III where $a=1, b=1$ at $[M+H]^+=367.2$.

EXAMPLE 11

The product from Example 1 is dissolved in water to give an aqueous solution of 5 g of the acid in 25 ml of water. To this is added p-anisidine in aqueous acetone until the pH of the solution is 7. This solution is evaporated to dryness, and the solid obtained is recrystallised twice from isopropanol. The free acid is regenerated by dissolving the purified salt in aqueous NaOH and washing out the liberated amine with ether six times. Acidification of the aqueous layer to pH1 by addition of aqueous hydrochloric acid followed by evaporation gives a solid containing the purified product and sodium chloride. The sodium chloride is separated by addition of acetone and filtration. Evaporation of the acetone gives the purified product as a yellow solid. GPC analysis of the purified product shows only one peak, whereas the mixture obtained in Example 1 gives 4 peaks, corresponding to the four compounds identified by mass spectrometry. The product obtained after purification corresponds to a compound of formula II where $R_1$ to $R_6=H, x=1$ and $y=2$.

EXAMPLE 12

Example 7 is repeated using 3.7 g maleic anhydride and 22 g of 4-t-butyl-o-xylene with 0.24 g di-tert-butyl peroxide in place of the mixture used in Example 7. The yield of product is 3.3 g, 89% based on maleic anhydride. The product has $M_w=660, M_n=620$ and $M_w/M_n=1.07$.

COMPARATIVE EXAMPLE 50 g maleic anhydride are dissolved in 51.4 g of solvent mixture made up to 99% o-xylene and 1% m-xylene and heated to 130° C. 14.89 g di-tert butyl peroxide in 27.0 g of the same solvent are added over 15 minutes and the reaction mixture heated for 5 hours. The mixture is cooled to 70° C. and the top layer removed. 60 g of product is obtained (120% yield). The product has $M_w=890$ and $M_n=640$ giving $M_w/M_n=1.39$.

TEST EXAMPLES

The ability of the products in preventing the deposition of alkaline earth metal salts is measured by mixing together solutions containing the respective cations and anions to give a solution which precipitates under the conditions specified. 2 ppm of the products are added to the cation solution before mixing. After a certain period of time the concentration of the cation left in solution is measured and the % inhibition of precipitation (I %) is calculated using the formula:

$$I\% = \frac{C_{final} - C_{blank}}{C_{initial} - C_{blank}} \times 100$$

where
C final = cation concentration at end of test
C initial = cation concentration at start of test
C blank = cation concentration at end of test in absence of a threshold agent Agents showing I%>50% are considered suitable for the prevention of deposits.

CALCIUM CARBONATE INHIBITION

Conditions: $Ca^{2+}$ 150 mg/l, $Mg^{2+}$ 45 mg/l, $CO_3^{2-}$ 51 mg/l, $HCO_3^-$ 269 mg/l, 70° C., 30 minutes, additive dose 2 mg/l.

The results obtained are:

| Additive | % Inhibition |
|---|---|
| Product from Example 1 | 93 |
| Product from Example 6 | 83 |
| Product from Example 7 | 82 |
| Product from Example 8 | 89 |
| Product from Example 9 | 88 |
| Product from Example 10 | 93 |
| Product from Example 11 | 95 |
| Product from Example 12 | 93 |
| Product from Comparative Example | 66 |
| Commercial Polyacrylate, molecular weight 2000 | 67 |

These results show that while the product from the comparative example and the commercial polyacrylate are active threshold agents, the products of the Examples are significantly better.

85° C. SEEDED CALCIUM CARBONATE INHIBITION TEST

This test assesses the ability of additives to inhibit the precipitation of calcium carbonate under seeded growth conditions.

The test solution contains 125 mg/l $Ca^{2+}$, 375 mg/l $Mg^{2+}$, 182 mg/l $CO_3^{2-}$ and 2 mg/l additive. Each test solution contains 0.02 g dry calcium carbonate seeds. The test is conducted for 30 minutes at 85° C. and the level of $Ca^{2+}$ ions in solution measured. The results, which clearly show the superior activity of the product of Example 1, are:

| Additive | % Inhibition |
|---|---|
| Product from Example 1 | 69 |
| Product from Comparative Example | 20 |
| Commercial Polyacrylate, molecular weight 2000 | 12 |

CALCIUM SULPHATE INHIBITION

The test solution contains 2940 mg/l $Ca^{2+}$, 7200 mg/l $SO_4^{2-}$, 7500 mg/l NaCl, pH 8.0–8.5. The test is conducted for 24 hours at 70° C. using 5 mg/l additive. The results obtained are:

| Additive | % Inhibition 5 mg/l |
|---|---|
| Product from Example 1 | 92 |
| Commercial Polyacrylate, molecular weight 2000 | 31 |
| Commercial polymaleic anhydride molecular weight 800 | 12 |

These results show the much higher activity of the product of Example 1.

BARIUM SULPHATE INHIBITION

This test uses natural sea-water and a synthetic formation water to simulate downwell conditions. The test solution contains 136.3 mg/l $Ba^{2+}$, 335.1 mg/l $Sr^{2+}$, 1666 mg/l $Ca^{2+}$ and 1380 mg/l $SO_4^{2-}$ and is buffered at pH 5.5. The test is conducted for 3 hours in a shaking water bath at 70° C. The concentration of $Ba^{2+}$ in solution is determined on completion of the test. An inhibition of 94% is obtained using 20 mg/l of the product of Example 1.

CALCIUM CARBONATE INHIBITION

Conditions: $Ca^{2+}$ 600 ppm, $Mg^{2+}$ 300 ppm, $HCO_3^-$ 600 ppm, 40° C., 24 hours, solutions stirred at 150 rpm. The results obtained are:

| Additive | % Inhibition |
|---|---|
| (A) Product from Example 6 (15 ppm) | 80 |
| (B) A (15 ppm) + copolymer of 6 moles maleic anhydride, 1 mole ethyl acrylate and 1 mole vinyl acetate (2.5 ppm) | 85.2 |

We claim:

1. A process for inhibiting the deposition of a scale-forming compound from water or an aqueous system which comprises
adding to the water or aqueous system a polymaleic anhydride having a weight average molecular weight by gel permeation chromatography of between 450 and 800 and a polydispersivity of between 1.0 and 1.15 and comprising at least one anhydride of formula II

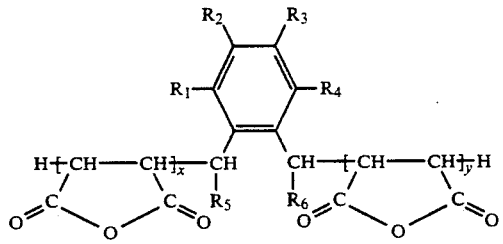

where
$R_1$, $R_2$, $R_3$ and $R_4$ each independently denote a hydrogen atom, a $C_1$–$C_4$ alkyl group or a carboxyl group;
$R_5$ and $R_6$ each independently denote a hydrogen atom or a methyl group, or $R_5$ and $R_6$ together denote a methylene or ethylene group;
x denotes 1, 2 or 3, and
y denotes 1, 2 or 3, with the proviso that x and y are not both 1; and
at least one anhydride of formula III

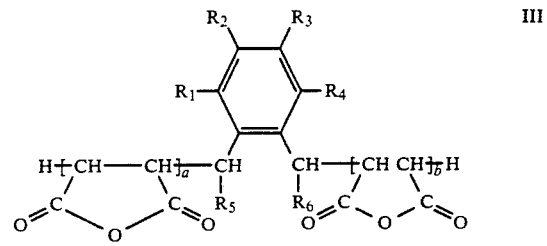

where
$R_1$, $R_2$, $R_3$, $R_4$, $R_5$ and $R_6$ are as defined above,
a and b each denote zero or 1, and
the sum of a+b is 1 or 2.

2. A process for inhibiting the deposition of a scale-forming compound from water or an aqueous system which comprises
adding to the water or aqueous system a polycarboxylic acid anhydride or a polycarboxylic acid or water-soluble salt formed by hydrolysis of said anhydride, said anhydride being of formula II

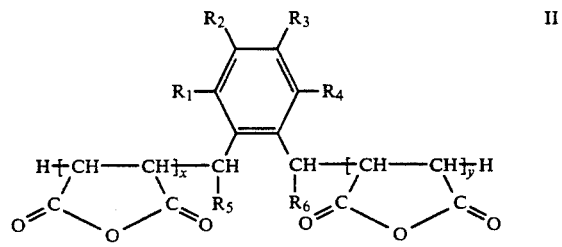

where
$R_1$, $R_2$, $R_3$ and $R_4$ each independently denote a hydrogen atom, a $C_1$–$C_4$ alkyl group or a carboxyl group;

$R_5$ and $R_6$ each independently denote a hydrogen atom or a methyl group, or $R_5$ and $R_6$ together denote a methylene or ethylene group;

x denotes 1, 2 or 3, and y denotes 1, 2 or 3, with the proviso that x and y are not both 1.

3. A process according to claim 2 where in the anhydride of formula II $R_1$ to $R_6$ each denote a hydrogen atom; or $R_1$ to $R_3$, $R_5$ and $R_6$ each denote a hydrogen atom and $R_4$ denotes a methyl group; or $R_1$ denotes a methyl group and $R_2$ to $R_6$ each denote a hydrogen atom; or $R_1$, $R_4$, $R_5$ and $R_6$ each denote a hydrogen atom and $R_2$ and $R_3$ each denote a methyl group; or $R_1$, $R_2$, $R_4$, $R_5$ and $R_6$ each denote a hydrogen atom and $R_3$ denotes a methyl group; or $R_1$, $R_3$, $R_4$, $R_5$ and $R_6$ each denote a hydrogen atom and $R_2$ denotes a methyl group; or $R_1$, $R_2$, $R_4$, $R_5$ and $R_6$ each denote a hydrogen atom and $R^3$ denotes a tert. butyl group; or $R_1$ and $R_3$ to $R_6$ each denote a hydrogen atom and $R_2$ denotes a tert. butyl group; or $R_1$, $R_1$, $R_3$, $R_5$ and $R_6$ each denote a hydrogen atom and $R_2$ and $R_4$ each denote a methyl group; or $R^1$ and $R^3$ each denote a methyl group and $R_2$, $R_4$, $R_5$ and $R_6$ each denote a hydrogen atom; or $R_1$, $R_4$, $R_5$ and $R_6$ each denote a hydrogen atom and $R_2$ and $R_3$ each denote a carboxyl group.

4. A process according to claim 3 where in the anhydride of formula II, x denotes 1 and y denotes 2.

5. A process according to claim 4 where in the anhydride of formula II, $R_1$ to $R_6$ each denote a hydrogen atom.

6. A process according to claim 2 in which said anhydride, polycarboxylic acid or salt is added together with an anhydride of formula III

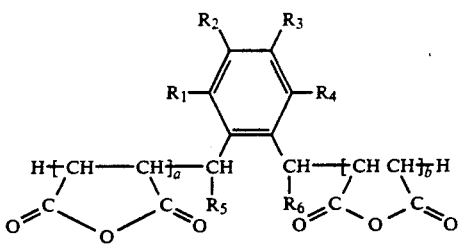

where $R_1$, $R_2$, $R_3$, $R_4$, $R_5$ and $R_6$ are as defined in claim 2, a and b each denote zero or 1, and the sum of a+b is 1 or 2, or a polycarboxylic acid or water-soluble salt formed by hydrolysis of the anhydride of formula III.

7. A process according to claim 3 in which said anhydride, polycarboxylic acid or salt is added together with an hydride of formula III

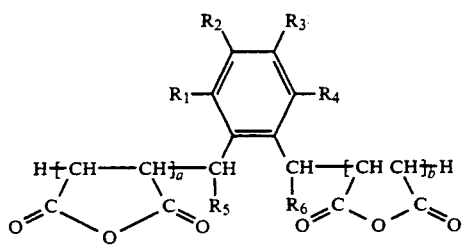

where $R_1$, $R_2$, $R_3$, $R_4$, $R_5$ and $R_6$ are as defined in claim 26, a and b each denote zero or 1, and the sum of a+b is 1 or 2, or a polycarboxylic acid or water-soluble salt formed by hydrolysis of the anhydride of formula III.

8. A process according to claim 6 where in the anhydride of formula II, x denotes 1 and y denotes 2.

9. A process according to claim 7 where in the anhydride of formula II, x denotes 1 and y denotes 2.

* * * * *